US008663091B2

(12) United States Patent
Diolaiti

(10) Patent No.: US 8,663,091 B2
(45) Date of Patent: Mar. 4, 2014

(54) MEDICAL ROBOTIC SYSTEM HAVING ENTRY GUIDE CONTROLLER WITH INSTRUMENT TIP VELOCITY LIMITING

(71) Applicant: Intuitive Surgical Operations, Inc., Sunnyvale, CA (US)

(72) Inventor: Nicola Diolaiti, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/847,584

(22) Filed: Mar. 20, 2013

(65) Prior Publication Data

US 2013/0218171 A1   Aug. 22, 2013

Related U.S. Application Data

(62) Division of application No. 12/163,069, filed on Jun. 27, 2008, now Pat. No. 8,414,469.

(51) Int. Cl.
*A61B 1/00* (2006.01)
*A61B 19/00* (2006.01)
*G06F 19/00* (2011.01)
*G05B 23/02* (2006.01)

(52) U.S. Cl.
CPC ............. *A61B 19/20* (2013.01); *A61B 19/22* (2013.01); *A61B 19/2203* (2013.01)
USPC ........... 600/114; 600/102; 600/104; 600/109; 600/117; 600/118; 606/130; 700/245; 700/57; 700/62; 318/568.25

(58) Field of Classification Search
USPC ................ 600/101, 104, 109, 114, 117–118; 318/568.1–568.25; 606/130; 700/56–66, 245–264
See application file for complete search history.

(56) References Cited

U.S. PATENT DOCUMENTS

| | | | |
|---|---|---|---|
| 5,511,147 A | 4/1996 | Abdel-Malek | |
| 6,092,004 A | 7/2000 | Harima | |
| 6,364,888 B1 * | 4/2002 | Niemeyer et al. | ............. 606/130 |
| 6,493,608 B1 | 12/2002 | Niemeyer | |
| 6,565,554 B1 | 5/2003 | Niemeyer | |
| 6,714,839 B2 | 3/2004 | Salisbury et al. | |
| 6,772,053 B2 | 8/2004 | Niemeyer | |
| 6,786,896 B1 | 9/2004 | Madhani et al. | |
| 6,799,065 B1 | 9/2004 | Niemeyer | |
| 7,025,064 B2 | 4/2006 | Wang et al. | |
| 7,155,315 B2 | 12/2006 | Niemeyer et al. | |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — John P Leubecker
*Assistant Examiner* — Arnaldo Torres Diaz

(57) ABSTRACT

A medical robotic system includes an entry guide with articulatable instruments extending out of its distal end, an entry guide manipulator providing controllable four degrees-of-freedom movement of the entry guide, and a controller configured to limit joint velocities in the entry guide manipulator so as to prevent movement of tips of the articulatable instruments from exceeding a maximum allowable linear velocity when the entry guide manipulator is being used to move the entry guide.

7 Claims, 10 Drawing Sheets

(56) References Cited

U.S. PATENT DOCUMENTS

| | | |
|---|---|---|
| 7,453,227 B2 | 11/2008 | Prisco et al. |
| 7,859,540 B2 | 12/2010 | Dariush |
| 8,414,469 B2 | 4/2013 | Diolaiti |
| 2002/0082612 A1* | 6/2002 | Moll et al. .................. 606/130 |
| 2003/0004610 A1 | 1/2003 | Niemeyer et al. |
| 2006/0106493 A1 | 5/2006 | Niemeyer et al. |
| 2007/0142968 A1 | 6/2007 | Prisco et al. |
| 2007/0287992 A1* | 12/2007 | Diolaiti et al. ................ 606/1 |
| 2009/0088775 A1 | 4/2009 | Swarup et al. |
| 2009/0222133 A1 | 9/2009 | Buckingham et al. |
| 2009/0326556 A1* | 12/2009 | Diolaiti et al. .............. 606/130 |
| 2010/0168919 A1 | 7/2010 | Okamoto |
| 2011/0276059 A1 | 11/2011 | Nowlin et al. |
| 2012/0109152 A1* | 5/2012 | Quaid, III .................. 606/130 |
| 2012/0143212 A1* | 6/2012 | Madhani et al. ............. 606/130 |
| 2013/0023899 A1* | 1/2013 | Green ........................ 606/130 |

* cited by examiner

MEDICAL ROBOTIC SYSTEM HAVING ENTRY GUIDE CONTROLLER WITH INSTRUMENT TIP VELOCITY LIMITING

CROSS REFERENCE TO RELATED APPLICATIONS

This application is a divisional of application Ser. No. 12/163069, filed Jun. 27, 2008, which is incorporated herein by reference.

FIELD OF THE INVENTION

The present invention generally relates to medical robotic systems and in particular, to a medical robotic system having articulatable instruments extending out of an entry guide and an entry guide controller for moving the entry guide without exceeding a maximum allowable linear velocity for tips of the articulatable instruments.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulatable camera and a plurality of articulatable surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

To properly guide the instruments to and maneuver them about a work site within a patient, an entry guide manipulator commandable through operator interaction with one or more input devices is desirable to move the entry guide through and about a pivot point at the entry aperture. In doing so, however, it is important for the safety of the patient and the instruments extending out of the distal end of the entry guide that the linear velocity of the instrument tips be controlled as the entry guide moves. Therefore, it is desirable to restrict the linear velocity of the instrument tips to a maximum allowable linear velocity.

OBJECTS AND SUMMARY OF THE INVENTION

Accordingly, one object of one or more aspects of the present invention is a method for positioning and orienting an entry guide that guides a camera and at least one surgical tool through a single entry aperture in a patient to a work site in the patient.

Another object of one or more aspects of the present invention is a method for moving an entry guide without exceeding a maximum allowable linear velocity of a tip of an articulatable instrument extending out of a distal end of the entry guide.

Another object of one or more aspects of the present invention is a medical robotic system including a controller for moving an entry guide without exceeding a maximum allowable linear velocity on movement of a tip of an articulatable instrument extending out of a distal end of the entry guide.

These and additional objects are accomplished by the various aspects of the present invention, wherein briefly stated, one aspect is a method for positioning and orienting an entry guide that guides a camera and at least one surgical tool through a single entry aperture in a patient to a work site within the patient, the method comprising: receiving an image referenced command indicative of a desired state of an image relative to eyes of an operator, wherein the image is derived from data provided by the camera and displayed on a display screen so as to be viewable by the operator; processing the image referenced command to generate a camera command so that a state of a tip of the camera provides the desired state of the image being displayed on the display screen; processing the camera command to generate an entry guide command so that a state of a distal tip of the entry guide provides the desired state of the image being displayed on the display screen; and processing the entry guide command to generate joint actuator commands so that an entry guide manipulator manipulates the entry guide so that the camera provides data from which the desired state of the image is derived.

Another aspect is a method for moving an entry guide without exceeding a maximum allowable linear velocity of a tip of an articulatable instrument extending out of a distal end of the entry guide, the method comprising: determining desired states of mechanical elements for effecting a desired state of the entry guide; determining a length that the tip of the articulatable instrument extends beyond the distal end of the entry guide; limiting the desired movements of the mechanical elements so as to avoid exceeding the maximum allowable linear velocity on the tip of the articulatable instrument; and commanding the mechanical elements to move in response to the limited desired movements of the mechanical elements.

Another aspect is a medical robotic system comprising: an entry guide; an entry guide manipulator for manipulating the entry guide relative to a remote center; a plurality of articulatable instruments extending through the entry guide and out of a distal end of the entry guide, the plurality of articulatable instruments including an articulatable camera; an input device; and a controller configured to control movement of the entry guide through the entry guide manipulator in response to movement of the input device without exceeding a maximum allowable linear velocity of tips of the plurality of articulatable instruments.

Another aspect is a method for positioning and orienting an entry that guides a camera to a work site, comprising: processing and displaying images periodically captured by the camera on a display screen; disassociating a first input device from a first articulatable tool, and disassociating a second input device from a second articulatable tool; associating the first and second input devices with the entry guide; generating an image referenced control from translational movement of the first and second input devices; positioning and orienting the entry guide in response to the image referenced command; maintaining orientational alignment between the first input device and the first articulatable tool by feeding back information of an orientation of the first articulatable tool back to the first input device so as to cause orientational movement of the first input device when the first input device and the first articulatable tool are orientationally out of alignment, and maintaining orientational alignment between the second input device and the second articulatable tool by feeding back information of an orientation of the second articulatable tool back to the second input device so as to cause orientational movement of the second input device when the second input device and the second articulatable tool are orientationally out of alignment; disassociating the first and second input devices from the entry guide; and re-associating the first input device with the first articulatable tool, and re-associating the second input device with the second articulatable tool.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
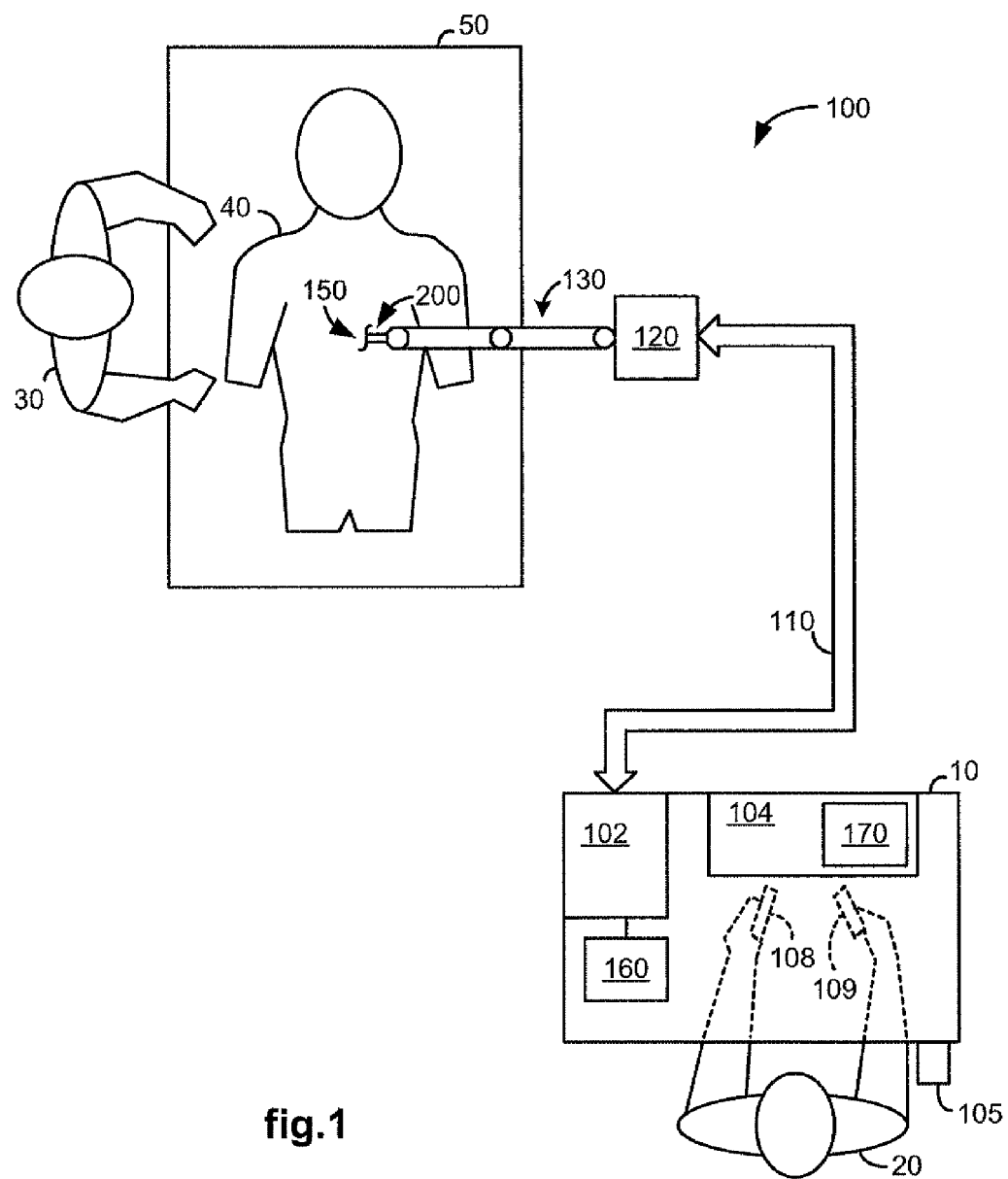
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

Figure 5:
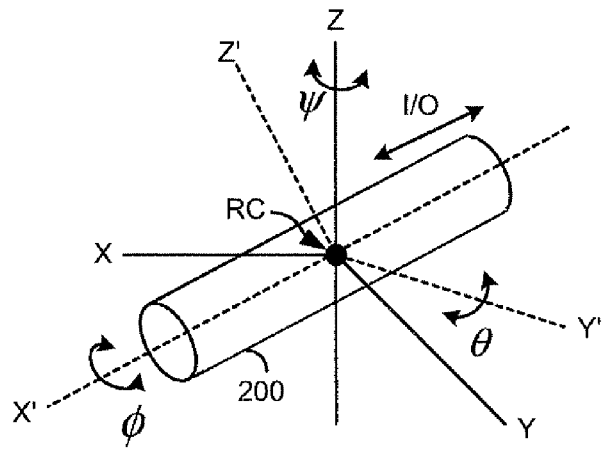
FIG. 5 illustrates a perspective view of an entry guide along with four degrees-of-freedom movement as used in a medical robotic system utilizing aspects of the present invention.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw about a pivot point located at the entry aperture 150. An example of such an entry guide manipulator is the entry guide manipulator 202 of FIG. 2 and an example of the four degrees-of-freedom movement that it manipulates the entry guide 200 with is shown in FIG. 5.

The console 10 includes a 3-D monitor 104 for displaying a 3-D image of a surgical site to the Surgeon, left and right hand-manipulatable input devices 108, 109, and a processor (also referred to herein as a "controller") 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160 and a Graphical User Interface (GUI) 170.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
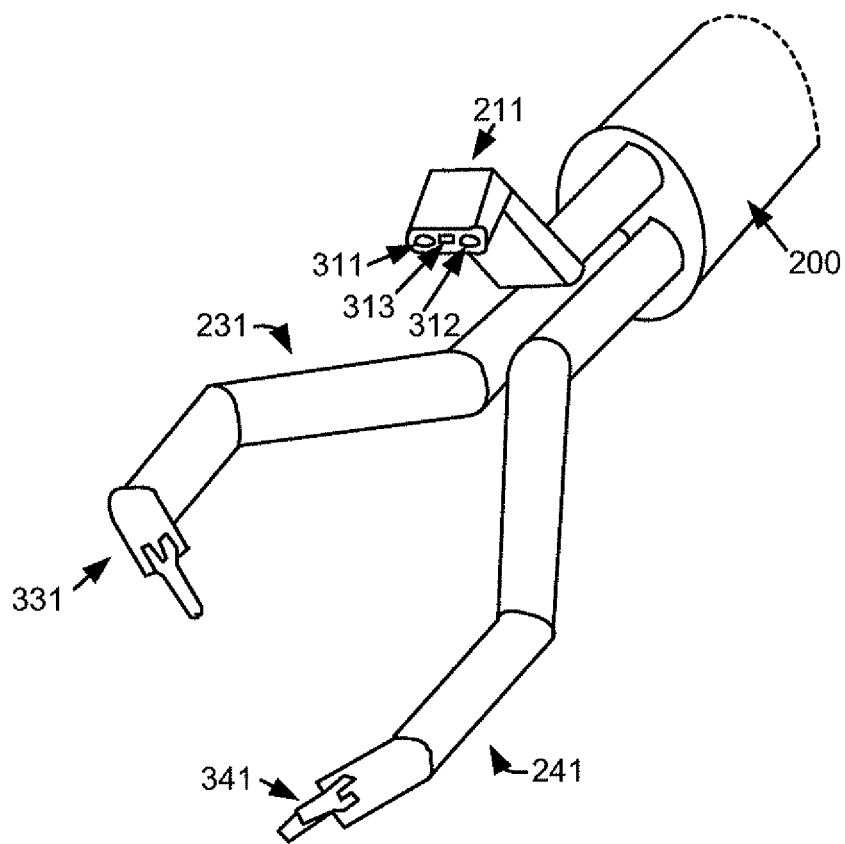
FIG. 3 illustrates a perspective view of a distal end of an entry guide with a plurality of articulatable instruments extending out of it, as used in a medical robotic system utilizing aspects of the present invention.
Figure 4:
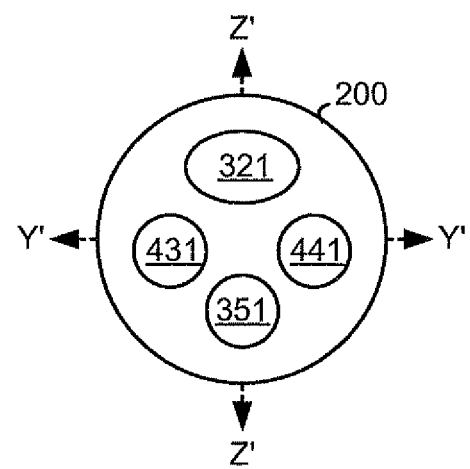
FIG. 4 illustrates a cross-sectional view of an entry guide as used in a medical robotic system utilizing aspects of the present invention.

As shown in FIG. 3, the entry guide 200 has articulatable instruments such as articulatable surgical tools 231, 241 and an articulatable stereo camera 211 extending out of its distal end. The camera has a pair of stereo image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. For example, as shown in FIG. 4, a passage 351 is available for extending another articulatable surgical tool through the entry guide 200 and out through its distal end. Each of the surgical tools 231, 241 is associated with one of the input devices 108, 109 in a tool following mode. The Surgeon performs a medical procedure by manipulating the input devices 108, 109 so that the controller 102 causes corresponding movement of their respectively associated surgical tools 231, 241 while the Surgeon views the work site in 3-D on the console monitor 104 as images of the work site are being captured by the articulatable camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 transforms the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate devices, such as the tools 231, 241, camera 211, and entry guide 200, that are selectively associated with the input devices 108, 109 at the time. Another function is to perform various methods and implement various controllers described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

Figure 2:
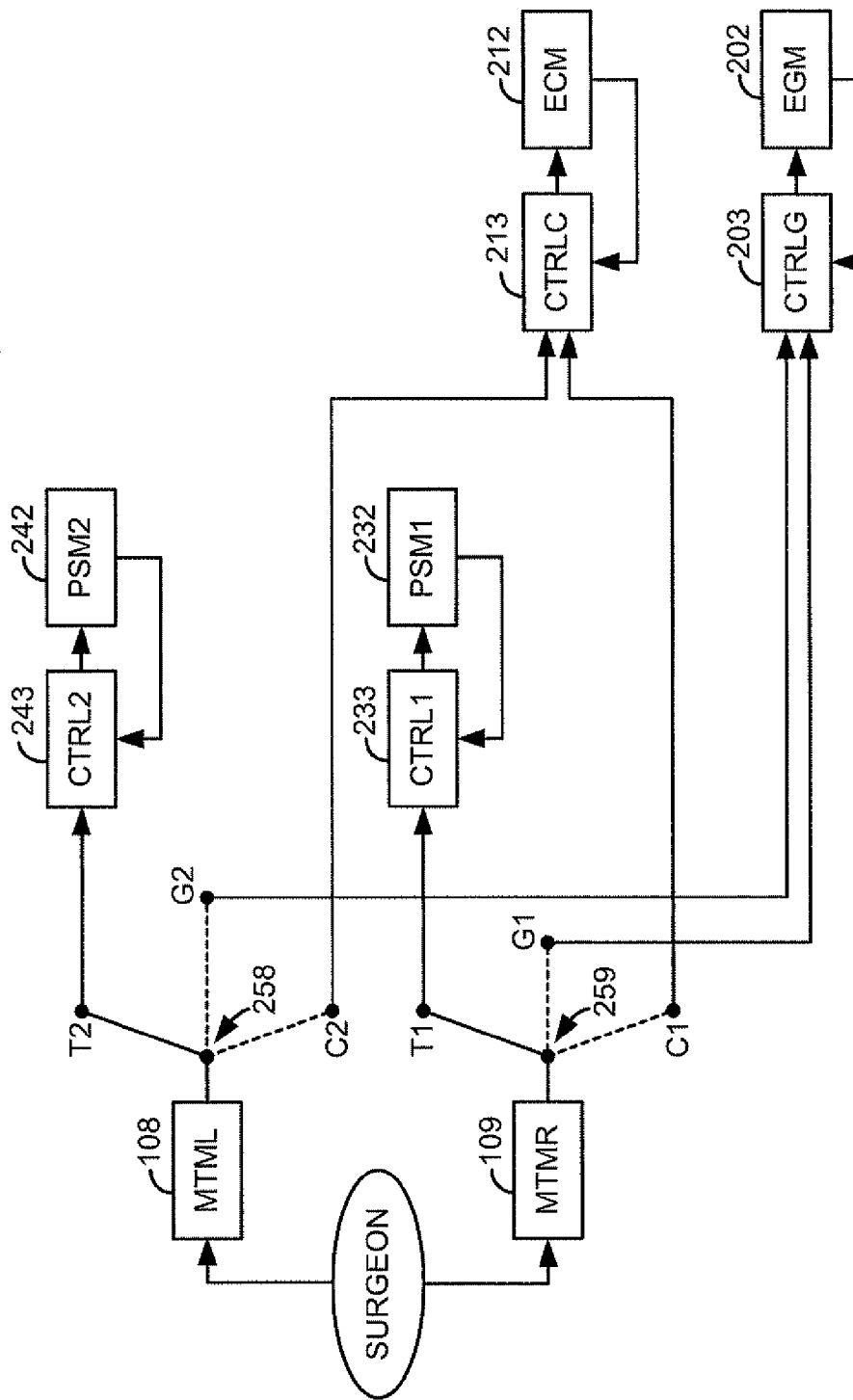
FIG. 2 illustrates a block diagram of components for controlling and selectively associating device manipulators to left and right hand-manipulatable input devices in a medical robotic system utilizing aspects of the present invention.

FIG. 2 illustrates, as an example, a block diagram of components for controlling and selectively associating device manipulators to the input devices 108, 109. Various surgical tools such as graspers, cutters, and needles may be used to perform a medical procedure at a work site within the Patient. In this example, two surgical tools 231, 241 are used to robotically perform the procedure and the camera 211 is used to view the procedure. The instruments 231, 241, 211 are inserted through passages in the entry guide 200. As described in reference to FIG. 1, the entry guide 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, and the entry guide 200 is manipulated by an entry guide manipulator (EGM) 202. So as to not overly encumber the figure, the devices 231, 241, 211, 200 are not shown, only their respective manipulators 232, 242, 212, 202 are shown in the figure.

Each of the instrument manipulators 232, 242, 212 is a mechanical assembly that carries actuators and provides a mechanical, sterile interface to transmit motion to its respective articulatable instrument. Each instrument 231, 241, 211 is a mechanical assembly that receives the motion from its manipulator and, by means of a cable transmission, propagates it to the distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams and belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

In contrast, the entry guide manipulator 202 has a different construction and operation. A description of the parts and operation of the entry guide manipulator 202 is described below in reference to FIG. 6.

In this example, each of the input devices 108, 109 may be selectively associated with one of the devices 211, 231, 241, 200 so that the associated device may be controlled by the input device through its controller and manipulator. For example, by placing switches 258, 259 in their respective tool following modes "T2" and "T1", the left and right input devices 108, 109 may be respectively associated with the first and second surgical tools 231, 241, which are telerobotically controlled through their respective controllers 233, 243 (preferably implemented in the processor 102) and manipulators 232, 242 so that the Surgeon may perform a medical procedure on the Patient while the entry guide 200 is locked in place.

When the camera 211 or the entry guide 200 is to be repositioned by the Surgeon, either one or both of the left and right input devices 108, 109 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is locked in place relative to the entry guide 200 by its controller. For example, by placing switches 258, 259 respectively in camera positioning modes "C2" and "C1", the left and right input devices 108, 109 may be associated with the camera 211, which is telerobotically controlled through its controller 213 (preferably implemented in the processor 102) and manipulator 212 so that the Surgeon may position the camera 211 while the surgical tools 231, 241 and entry guide 200 are locked in place by their respective controllers 233, 243, 203. If only one input device is to be used for positioning the camera, then only one of the switches 258, 259 is placed in its camera positioning mode while the other one of the switches 258, 259 remains in its tool following mode so that its respective input device may continue to control its associated surgical tool.

On the other hand, by placing switches 258, 259 respectively in entry guide positioning modes "G2" and "G1", the left and right input devices 108, 109 may be associated with the entry guide 200, which is telerobotically controlled through its controller 203 (preferably implemented in the processor 102) and manipulator 202 so that the Surgeon may position the entry guide 200 while the surgical tools 231, 241 and camera 211 are locked in place relative to the entry guide 200 by their respective controllers 233, 243, 213. As with the camera positioning mode, if only one input device is to be used for positioning the entry guide, then only one of the switches 258, 259 is placed in its entry guide positioning mode while the other one of the switches 258, 259 remains in its current mode.

The selective association of the input devices 108, 109 to other devices in this example may be performed by the Surgeon using the GUI 170 or the voice recognition system 160 in a conventional manner. Alternatively, the association of the input devices 108, 109 may be changed by the Surgeon depressing a button on one of the input devices 108, 109 or depressing the foot pedal 105, or using any other well known mode switching technique.

As shown in a perspective view of the entry guide 200 in FIG. 5, the entry guide 200 is generally cylindrical in shape and has a longitudinal axis X' running centrally along its length. The pivot point, which is also referred to as a remote center "RC", serves as an origin for both a fixed reference frame having X, Y and Z axes as shown and an entry guide reference frame having X', Y' and Z' axes as shown. When the system 100 is in the entry guide positioning mode, the entry guide manipulator 202 is capable of pivoting the entry guide 200 in response to movement of one or more associated input devices about the Z axis (which remains fixed in space) at the remote center "RC" in yaw ψ. In addition, the entry guide manipulator 202 is capable of pivoting the entry guide 200 in response to movement of the one or more input devices about the Y' axis (which is orthogonal to the longitudinal axis X' of the entry guide 200) in pitch θ, capable of rotating the entry guide 200 about its longitudinal axis X' in roll Φ, and linearly moving the entry guide 200 along its longitudinal axis X' in insertion/retraction or in/out "I/O" directions in response to movement of the one or more associated input devices. Note that unlike the Z-axis which is fixed in space, the X' and Y' axes move with the entry guide 200.

Figure 6:
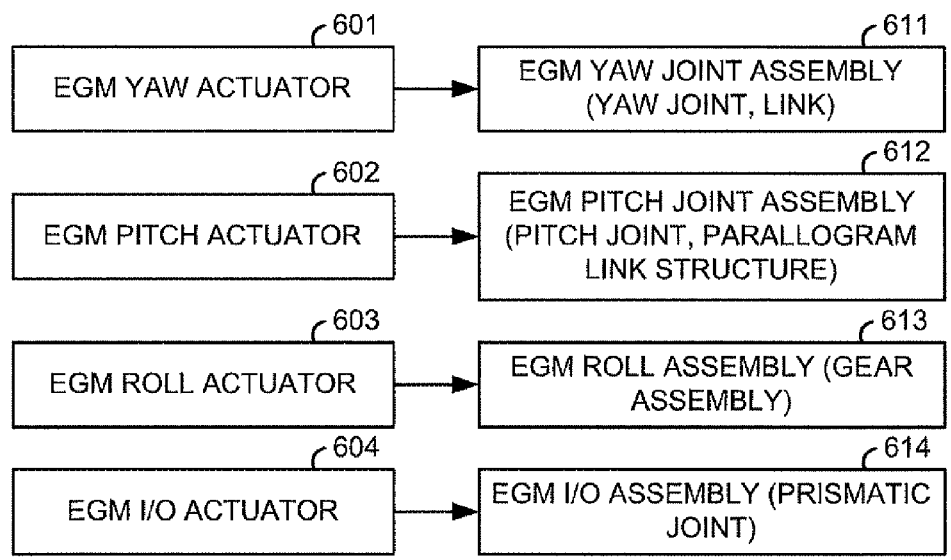
FIG. 6 illustrates a block diagram of interacting components of an entry guide manipulator as used in a medical robotic system utilizing aspects of the present invention.

As shown in FIG. 6, the entry guide manipulator (EGM) 202 has four actuators 601-604 for actuating the four degrees-of-freedom movement of the entry guide 200 (i.e., yaw ψ, pitch θ, roll Φ, and in/out I/O) and four corresponding assemblies 611-614 to implement them.

The EGM yaw assembly 611 includes a yaw rotary joint which is a part of the robotic arm assembly 130 that maintains its coordinate position in three-dimensional space while the entry guide manipulator 202 moves the entry guide 200. The EGM yaw assembly 611 further includes one or more links that couple it through other parts of the entry guide manipulator 202 to the entry guide 200 so that when the EGM yaw actuator 601 (e.g., a motor) actuates (e.g., rotates) the yaw rotary joint, the entry guide 200 is rotated about the fixed Z-axis at the remote center RC in yaw ψ.

The EGM pitch assembly 612 includes a pitch rotary joint which is a part of the robotic arm assembly that moves with the entry guide 200. The EGM pitch assembly 612 further includes one or more links that couple it through other parts of the entry guide manipulator 202 to the entry guide 200 so that when the EGM pitch actuator 602 (e.g., a motor) actuates (e.g., rotates) the pitch rotary joint, the entry guide 200 is rotated about the Y'-axis at the remote center RC in pitch θ.

The EGM roll assembly 613 includes a gear assembly that couples the entry guide 200 to the EGM roll actuator 603 so that when the EGM roll actuator 603 (e.g., a motor) actuates (e.g., its rotor rotates), the entry guide 200 also rotates about its longitudinal axis X' in response.

The EGM I/O assembly 614, on the other hand, includes a prismatic joint that is coupled to the EGM I/O actuator 604 so that when the EGM I/O actuator 604 (e.g., a motor) actuates (e.g., its rotor rotates), the rotary action is transferred into a linear displacement of the entry guide 200 along its longitudinal axis X'.

Figure 7:
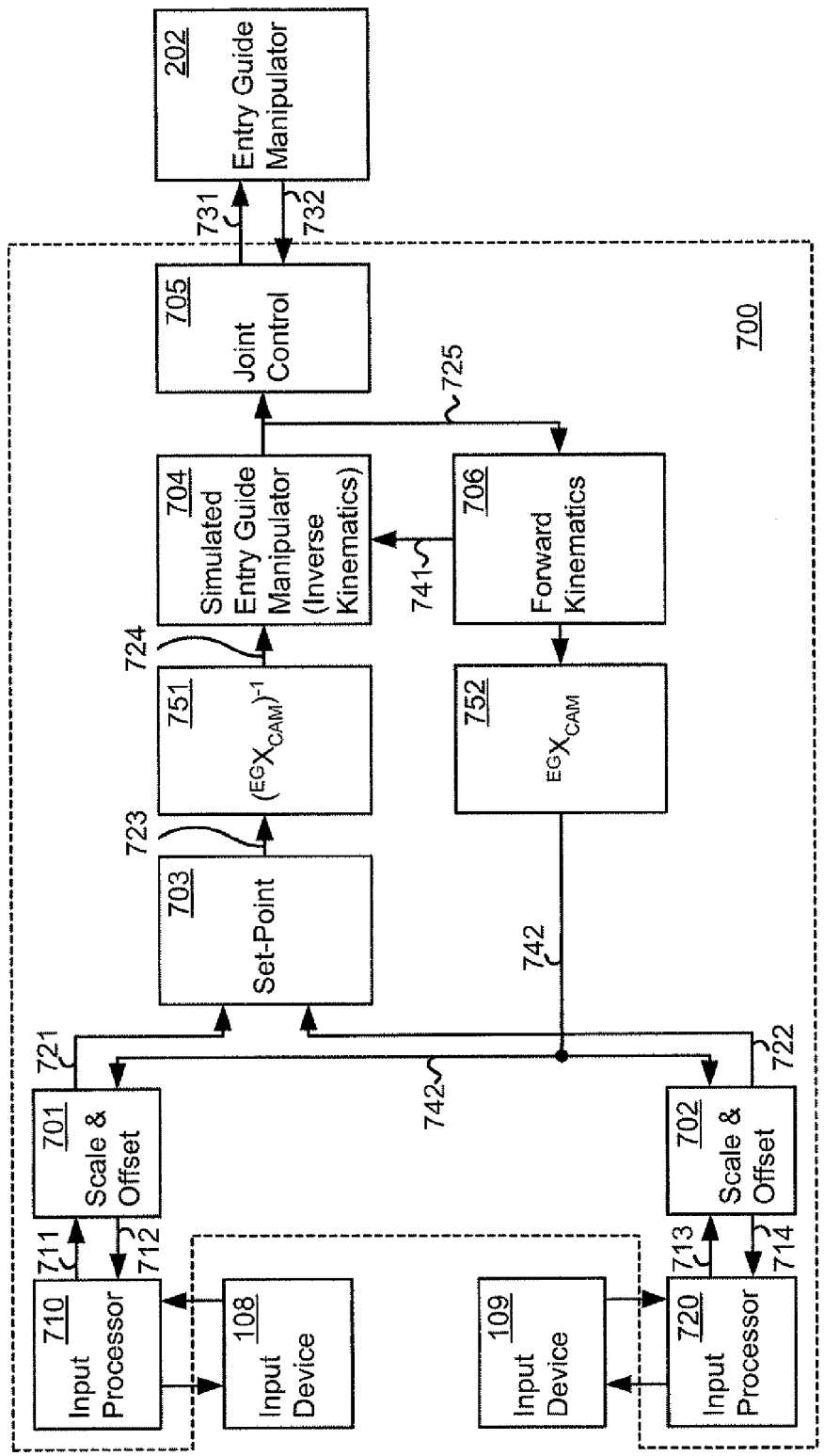
FIG. 7 illustrates a block diagram of an entry guide controller used to control an entry guide manipulator in a medical robotic system utilizing aspects of the present invention.

FIG. 7 illustrates, as an example, a block diagram of a controller 700 (which is one version of the controller 203) for controlling movement of the entry guide 200 in response to movement of the input devices 108, 109 when the input devices 108, 109 are selectively associated with the entry guide 200 in their respective entry guide positioning modes "G2" and "G1". In this example, both input devices 108, 109 are used to move the entry guide 200 as the Surgeon views images captured by the camera 211. The articulatable camera 211, which extends out of the distal end of the entry guide 200, is "soft" locked (through its controller 213) at its current position relative to the entry guide 200 during the entry guide positioning mode.

Thus, an image referenced control is implemented in the controller 700 so that the controller 700 controls movement of the entry guide 200 while the Surgeon is given the impression that he or she is moving the image captured by the camera 211. In particular, the Surgeon is provided with the sensation that he or she is grasping the image being displayed on the monitor 104 with his or her left and right hands and moving the image about the work site to a desired viewing point. Note that under this type of control, the image on the monitor 104 appears to move in opposite directions in response to movement of the input devices 108, 109. For example, the image moves to the right when the input devices 108, 109 are moved to the left (and vice versa) and the image moves up when the input devices 108, 109 are moved down (and vice versa).

The input devices 108, 109 include a number of links connected by joints so as to facilitate multiple degrees-of-freedom movement. For example, as the Surgeon moves the input devices 108, 109 from one position to another, sensors associated with the joints of the input devices 108, 109 sense such movement at sampling intervals (appropriate for the processing speed of the controller 102 and entry guide control purposes) and provide digital information indicating such sampled movement in joint space to input processing blocks 710, 720.

Figure 11:
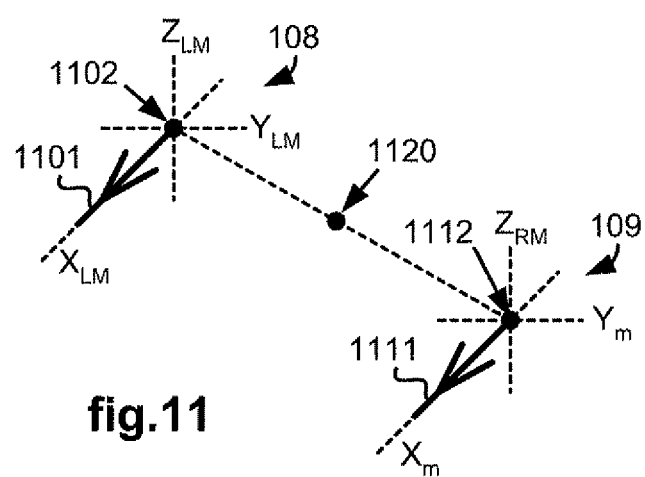
FIG. 11 illustrates reference frames for left and right input devices and a set-point defined between the input devices as used in a medical robotic system utilizing aspects of the present invention.

As shown in FIG. 11, each of the input devices 108, 109 has a pivot point (also referred to herein as a "control point") and a reference frame centered at the pivot point. The input devices 108, 109 provide three translational degrees-of-freedom movement (e.g., forward/back along their respective longitudinal axes $X_{LM}$, $X_{RM}$ of their grippers 1101, 1111; side-to-side along first axes $Y_{LM}$, $Y_{RM}$ orthogonal to the longitudinal axes $X_{LM}$, $X_{RM}$; and up/down along second axes $Z_{LM}$, $Z_{RM}$ orthogonal to the first axes $Y_{LM}$, $Y_{RM}$ and longitudinal axes $X_{LM}$, $X_{RM}$) for their respective pivot points 1102, 1112 of their grippers 1101, 1111. The input devices 108, 109 also provide three orientational degrees-of-freedom movement (e.g., roll about their respective longitudinal axes $X_{LM}$, $X_{RM}$; pitch about their respective first axes $Y_{LM}$, $Y_{RM}$; and yaw about their respective second axes $Z$, $Z_{RM}$) for their respective pivot points 1102, 1112 of their grippers 1101, 1111. In addition, squeezing their respective grippers 1101, 1111 may provide additional degrees-of-freedom for manipulating end effectors of surgical tools respectively associated with the input devices 108, 109 at the time.

Input processing blocks 710, 720 process the information received from the joint sensors of the input devices 108, 109 to transform the information into corresponding desired positions and velocities for the image being displayed on the monitor 104 in a Cartesian space relative to a reference frame associated with the Surgeon's eyes (the "eye reference frame") by computing, for example, joint velocities from the joint position information or, alternatively, using velocity sensors) and performing the transformation using a Jacobian matrix and eye related information using well-known transformation techniques.

Scale and offset processing blocks 701, 702 receive the processed information 711, 713 from the input processing blocks 710, 720, convert the desired positions and velocities to camera tip positions and velocities in the reference frame of the entry guide 200, and apply scale and offset adjustments to the information so that the resulting movement of the camera 211 and consequently, the image being viewed on the monitor 104 appears natural and as expected by the operator of the input devices 108, 109. The scale adjustment is useful where small movements of the camera 211 are desired relative to larger movement of the input devices 108, 109 in order to allow more precise movement of the camera 211 as it views the work site. To implement the shared control for moving the camera 211 by the input devices 108, 109, lateral offsets are applied to shift the control point to the left for the input device 108 which is being operated by the left hand of the operator and to the right for the input device 109 which is being operated by the right hand of the operator so that each of the input devices 108, 109 appears to control a corresponding view of the stereoscopic image being displayed on the monitor 104. In addition, offset adjustments are applied for aligning the input devices 108, 109 with respect to the Surgeon's eyes as he or she manipulates the input devices 108, 109 to command movement of the camera 211 and consequently, its captured image that is being displayed at the time on the monitor 104.

The outputs 721, 722 of the scale and offset blocks 701, 702 are provided to a set-point generation block 703 so that a single set of position and velocity commands for the camera tip 311 in the reference frame of the entry guide 200 is provided for the entry guide manipulator 202. Therefore, as the operator moves the input devices 108, 109, he or she forces a motion on the mid-point of what feels like to the operator to be a "virtual handlebar". This motion is then "transferred" to subsequent blocks of the controller 700 as a set-point for Cartesian motions.

Up to this point, the controller 700 has treated the operator movement of the input devices 108, 109 as commanding a corresponding movement of the camera 211 using image referenced control. Ultimately, however, it is the entry guide manipulator 202, not the camera manipulator 213 that is to be moved in response to the operator commands. Therefore, an inverse "entry guide-to-camera" transform $(^{EG}X_{CAM})^{-1}$ block 751 converts the desired movement of the tip of the camera 211 into a desired movement of the tip of the entry guide 202 while still in the reference frame of the entry guide.

A simulated entry guide manipulator block 704 receives the output 724 of the inverse "entry guide-to-camera" transform $(^{EG}X_{CAM})^{-1}$ block 751 and transforms the commanded position and velocity for the distal end of the entry guide 200 from its Cartesian space to corresponding desired joint positions and velocities for the entry guide manipulator (EGM) 202 (e.g., EGM joint space) using the known inverse kinematics of the entry guide manipulator 202 and characteristics of the entry guide 200. In doing so, the simulated entry guide manipulator block 704 avoids singularities and limits the commanded joint positions and velocities to avoid physical limitations. In addition, it implements a method for moving the entry guide 200 without exceeding a velocity limit of a tip of an articulatable surgical instrument extending out of a distal end of the entry guide 200 as described in reference to FIG. 8.

The output 725 of the simulated entry guide manipulator block 704 is then provided to an EGM joint controller block 705 and a forward kinematics block 706. The joint controller block 705 includes a joint control system for each controlled joint (i.e., each mechanical element controlling one of the four degrees-of-freedom described in reference to FIG. 5) of the entry guide manipulator 202, and the output 725 of the simulated entry guide manipulator block 704 provides, as its inputs, the commanded value for each joint of the entry guide manipulator 202. For feedback control purposes, sensors associated with each of the controlled joints of the entry guide manipulator 202 provide sensor data 732 back to the joint controller block 705 indicating the current position and/or velocity of each joint of the entry guide manipulator 202. The sensors may sense this joint information either directly (e.g., from the joint on the entry guide manipulator 202) or indirectly (e.g., from the actuator in the entry guide manipulator 202 driving the joint). Each joint control system in the joint controller 705 then generates torque or other appropriate commands for its respective actuator (e.g., motor) in the entry guide manipulator 202 so as to drive the difference between the commanded and sensed joint values to zero in a conventional feedback control system manner.

The forward kinematics block 706 transforms the output 725 of the simulated entry guide manipulator block 704 from joint space back to the Cartesian space of the entry guide manipulator 202 using the forward kinematics of the entry guide manipulator 202. The output of the forward kinematics block 706 is then translated in an "entry guide-to-camera" transformation $(^{EG}X_{CAM})$ block 752 so that the controller 700 operates once again in camera referenced control mode.

The scale and offset blocks 701, 702 perform an inverse scale and offset functions on the output 742 of the "entry guide-to-camera" transformation ($^{EG}X_{CAM}$) block 752 (as well as performing a reversal of the set-point generation) before passing their respective outputs 712, 714 to the input processing blocks 710, 720 where error values are calculated between their respective outputs 711, 713 and inputs 712, 714. If no limitation or other constraint had been imposed on the input 724 to the simulated entry guide manipulator block 704, then the calculated error values would be zero. On the other hand, if a limitation or constraint had been imposed, then the error value is not zero and it is converted to a torque command that drives actuators in the input devices 108, 109 to provide force feedback felt by the hands of their operator. Thus, the operator becomes aware that a limitation or constraint is being imposed by the force that he or she feels resisting his movement of the input devices 108, 109 in that direction. In addition to this force feedback, forces coming from other sensors or algorithms may be superimposed on the force feedback.

An output 741 of the forward kinematics block 706 may also be provided to the simulated entry guide manipulator block 704 for control purposes. For example, the simulated position output may be fed back and compared with the commanded position.

Figure 8:
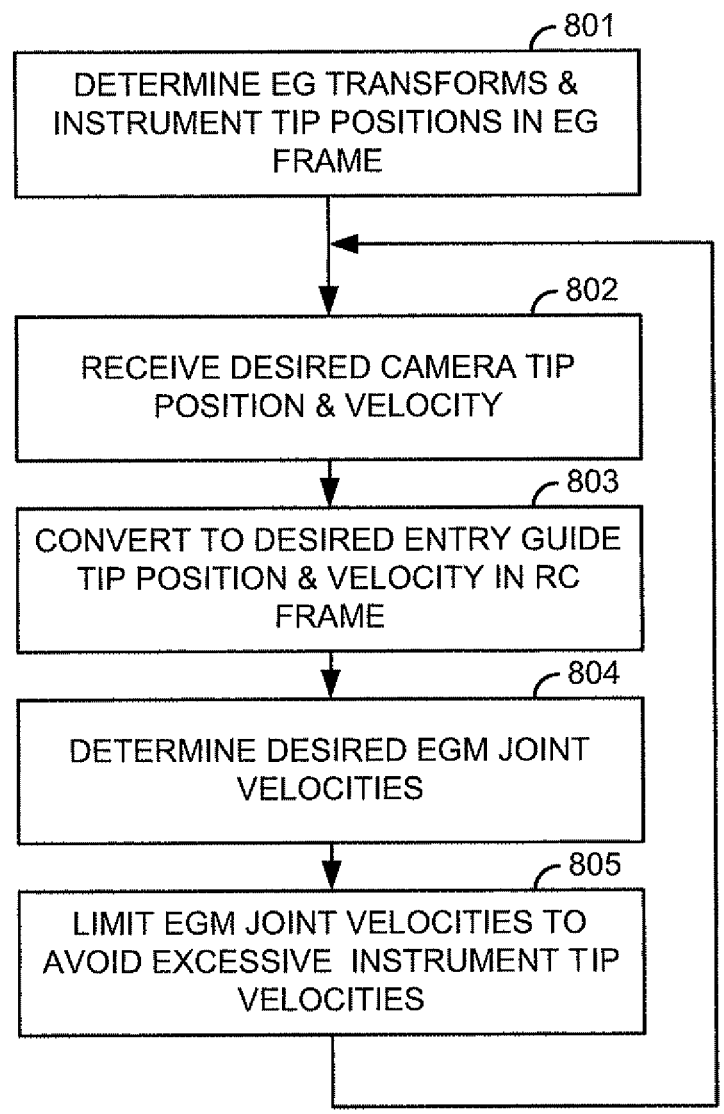
FIG. 8 illustrates a flow diagram of a method for moving an entry guide without exceeding a maximum allowable linear velocity on movement of a tip of an articulatable instrument extending out of a distal end of the entry guide, utilizing aspects of the present invention.

FIG. 8 illustrates, as an example, a flow diagram of a method, which may be implemented in the controller 700, for moving the entry guide 200 without exceeding a maximum allowable linear velocity on movement of a tip of an articulatable instrument (e.g., 211, 231 and 241 in FIG. 3) extending out of a distal end (e.g., tip) of the entry guide 200. Note that unlike a position limit which would prevent reaching positions beyond the limit, a velocity limit does not restrict the set of reachable positions but forces the Surgeon to perform potentially dangerous motions in a slower way.

Figure 10:
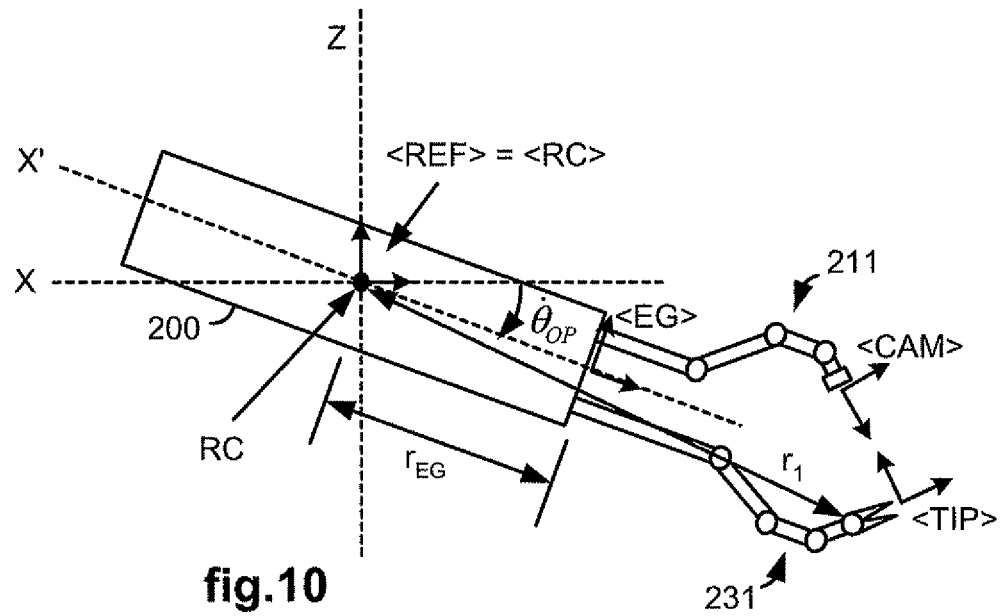
FIG. 10 illustrates a side view of an entry guide with various reference frames and measurements indicated thereon as used in a medical robotic system utilizing aspects of the present invention.

In applying the method, a number of reference frames is used. On the input side, the Surgeon views an image captured by the camera 211 on the console monitor 104 while the Surgeon controls the input devices 108, 109 to move the effectively image and consequently, in the entry guide positioning mode "G", the entry guide 200 (using image referenced control). Thus, an eye reference frame <EYE> is used on the input side that is based upon the position of the Surgeon's eyes as the Surgeon views the monitor 104 and manipulates the input devices 108, 109. On the entry guide side, as shown in FIG. 10, a camera reference frame <CAM> represents what the Surgeon is seeing at the time on the monitor 104, an entry guide tip reference frame <EG> represents what the controller 700 controls in entry guide positioning mode "G", an articulatable instrument tip reference frame <TIP> represents what needs to be velocity limited, and a remote center reference frame <REF> represents a fixed reference frame.

In 801, the method first determines transforms that relate the tip (i.e., distal end) of the entry guide 200 to the tips of each of the instruments 211, 231, 241 that are extending out of the distal end of the entry guide 200. Mathematically such transforms may be represented as follows for the present example: $^{EG}X_1$ for the first surgical tool 231, $^{EG}X_2$ for the second surgical tool 241, and $^{EG}X_{CAM}$ for the camera 211.

Figure 12:
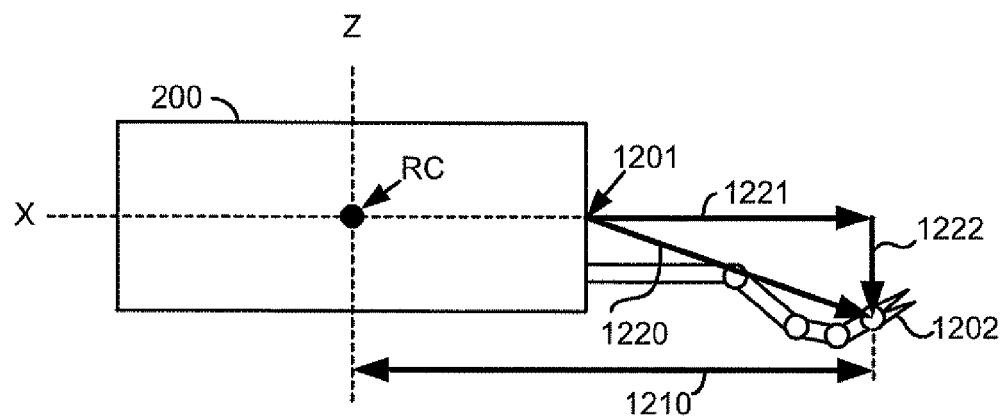
FIG. 12 illustrates a side view of an entry guide with various vectors indicated thereon as used in a medical robotic system utilizing aspects of the present invention.

The method then decomposes the positions of the instruments 211, 231, 241 into radial and tangential components with respect to the tip of the entry guide 200. For example, as shown in FIG. 12, a position 1220 of a tip 1202 of an instrument to the distal end 1201 of the entry guide 200 is shown decomposed into a radial component 1221 and tangential component 1222. Mathematically, this may be represented as follows for the three instruments:

$$^{EG}\vec{P}_1 = {}^{EG}\vec{P}_{1,RAD} + {}^{EG}\vec{P}_{1,TAN}$$

$$^{EG}\vec{P}_2 = {}^{EP}\vec{P}_{2,RAD} + {}^{EG}\vec{P}_{2,TAN}$$

$$^{EG}\vec{P}_{CAM} = {}^{EP}\vec{P}_{CAM,RAD} + {}^{EG}\vec{P}_{CAM,TAN}$$

Weight coefficients "α", based upon some criteria, may be assigned to each of the instruments to increase its effect in limiting the entry guide manipulator (EGM) 202 joint velocities. One criterion, for example, may be that instruments having end effectors or tips falling outside of the field of view of the camera 211 can have a larger weight coefficient and thus a larger impact on controlling EGM joint velocities. Another criterion, may be the distance that the instruments are from a specified part of the patient's anatomy (e.g., if CRT scans are available that may be registered to the patient, a certain area can be marked as delicate and thus the weighting coefficients of the instruments can be increased as they approach it). Mathematically, this may be represented as follows for three instruments:

$$^{EG}\vec{P}_{W1} = \alpha_1 {}^{EG}\vec{P}_1$$

$$^{EG}\vec{P}_{W2} = \alpha_2 {}^{EG}\vec{P}_2$$

$$^{EG}\vec{P}_{WCAM} = \alpha_{CAM} {}^{EG}\vec{P}_{WCAM,RAD} + {}^{EG}\vec{P}_{WCAM,TAN}$$

Note that the weighting factor for the camera is computed according to a slightly different criterion than the other instruments. In particular, the camera's weighting factor accounts for the camera tip's extension along the I/O direction and its elevation above that axis (i.e., how much it is "joggled up"). This is because the distal articulations of the camera instrument 211 (which are invisible to the user) might touch tissues as the camera tip 311 is moved.

In 802, the method receives a desired camera tip Cartesian position and velocity, such as the output 723 which is received by the inverse "entry guide-to-camera" transform $(^{EG}X_{CAM})^{-1}$ block 751 from the set-point generation block 703 of the controller 700.

In 803, the method converts the received desired camera tip Cartesian position and velocity to a corresponding desired entry guide tip (i.e., distal end) position and velocity, such as performed by the inverse "entry guide-to-camera" transform $(^{EG}X_{CAM})^{-1}$ block 751 to generate its output 724. The method then translates the desired entry guide tip position and velocity to the remote center reference frame using known geometries of the entry guide 200, such as may be performed in the simulated entry guide manipulator block 704 of the controller 700.

In 804, the method determines desired joint velocities for the entry guide manipulator 202 from the desired entry guide tip position and velocity in the remote center reference frame using known kinematics of the entry guide manipulator 202, such as may be performed in the simulated entry guide manipulator block 704 of the controller 700. In example, four joint velocities for the entry guide manipulator 202 are determined, one for each of the four degrees of freedom, i.e., desired yaw, pitch, I/O and roll joint velocities (where the term "joint" is understood herein to mean a mechanical element used to effectuate the degree-of-freedom).

In 805, the method limits the desired EGM joint velocities to avoid excessive instrument tip velocities. One technique for doing so is described in reference to FIG. 9 herein. In addition, the method also ensures that physical limitations on the EGM joints are not exceeded before generating position and velocity commands to drive the joints of the entry guide manipulator 202, such as done in the simulated entry guide manipulator block 704 of FIG. 7.

After completing 805, the method then loops back to 802 to process a next sampled movement of the input devices 108, 109 through 802-805. In this case, the positions and orientations of the instruments 211, 231, 241 are presumed to be "soft-locked" in place by their respective controllers during the entry guide positioning mode "G". Therefore, the transforms and positions determined in 801 relative to the entry guide 200 remain constant and need not be re-determined.

Figure 9:
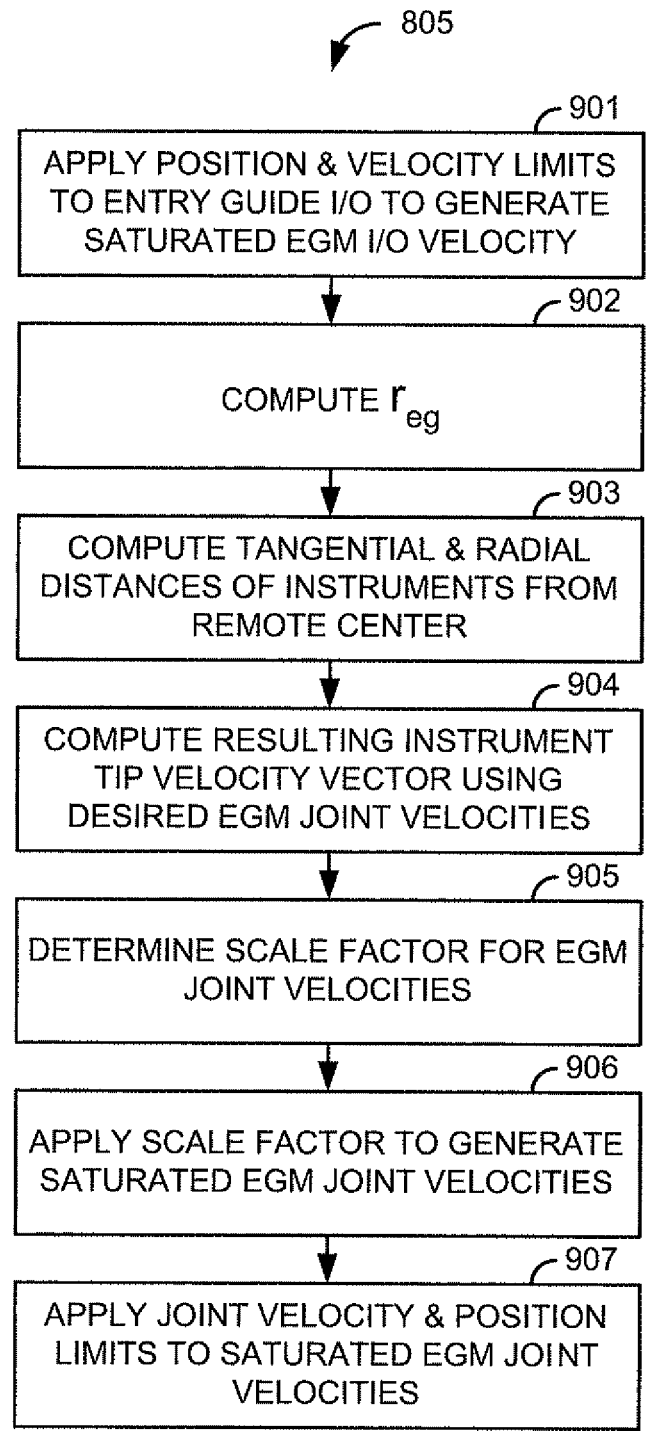
FIG. 9 illustrates a flow diagram of a method for limiting entry guide manipulator joint velocities to avoid excessive instrument tip velocities as used in a medical robotic system utilizing aspects of the present invention.

FIG. 9 illustrates, as an example, a flow diagram of a method, which is implemented in the simulated entry guide manipulator 704 of FIG. 7, for limiting entry guide manipulator joint velocities to avoid excessive instrument tip velocities. As previously mentioned, the method is particularly useful for performing 805 of FIG. 8.

In the present example, four EGM joint velocities are to be limited—the yaw, pitch, roll and I/O as shown and described in reference to FIG. 5. Of these joint velocities, only the I/O results in the same velocity for the entry guide tip and the instrument tip. In pitch and yaw, the instrument tip velocities are larger than the entry guide tip velocity because of the larger radius of rotation about the remote center (see, e.g., $r_1$ vs. $r_{EG}$ in FIG. 10). In roll, the tangential component of the instrument tip position needs to be taken into account as a contributor to the instrument tip velocity (see, e.g., tangential component 1222 in FIG. 12).

Figure 14:
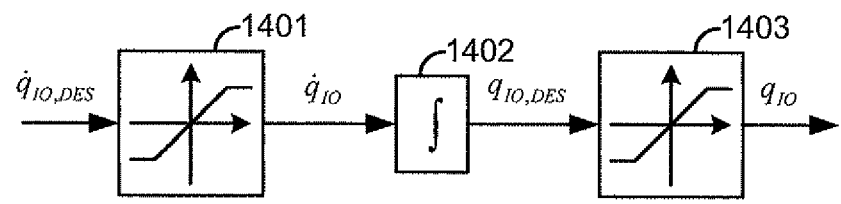
FIG. 14 illustrates a block diagram of an entry guide manipulator in/out (I/O) joint velocity and position limiting as used in a medical robotic system utilizing aspects of the present invention.

Thus, in 901, the method first limits the desired movement of the EGM I/O joint to take advantage of the configuration of the entry guide 200 and the instruments 211, 231, 241 extending out of the distal end of the entry guide 200 as noted above. One technique for limiting the movement of the EGM I/O joint is described with the visual aid of FIG. 14. First, the desired EGM I/O joint velocity $\dot{q}_{IO,DES}$ is limited by a velocity limiter 1401 so that its output $\dot{q}_{IO}$ is less than or equal to the velocity limit of the instrument tips. An integrator 1402 integrates the output $\dot{q}_{IO}$ to generate a desired EGM I/O joint position $q_{IO,DES}$ which is limited by a position limiter 1403 so that its output $q_{IO}$ is less than or equal to a maximum allowable displacement of the EGM I/O joint.

In 902, the method determines the distance $r_{EG}$ of the entry guide tip from the remote center in a straightforward manner using the EGM I/O joint position $q_{IO}$, and in 903, the method determines the distances $|{}^{RC}\vec{P}_{W1}|$, $|{}^{RC}\vec{P}_{W2}|$ of the instruments from the remote center in a straightforward manner using the positions ${}^{EG}\vec{P}_{W1}$, ${}^{EG}\vec{P}_{W2}$ of the instruments relative to the entry guide tip (as previously determined in 801 of FIG. 8) and the distance $r_{EG}$ of the entry guide tip from the remote center (as determined in 902).

In 904, the method determines a resulting velocity $\vec{V}_{1,DES}$, $\vec{V}_{2,DES}$, $\vec{V}_{CAM,DES}$ for each of the instruments 231, 241, 211 using the desired EGM rotary joint velocities (as determined in 804 of FIG. 8) and the instrument tip position from the remote center (as determined in 903), such as in the following equation for the $i^{th}$ instrument:

$$\vec{V}_{i,DES} = J(q_{EG}, r_{i,RAD}) \begin{bmatrix} \dot{q}_{OY,DES} \\ \dot{q}_{OP,DES} \\ \dot{q}_{RO,DES} \end{bmatrix} + \hat{X}'_{EG} \dot{q}_{RO,DES} \times \vec{r}_{i,TAN}$$

where the term "$J(q_{EG}, r_{i,RAD})$" is the EGM Jacobian computed by replacing $q_{IO}$ (as determined in 901) with a value that would place the entry guide tip at a distance equal to the radial component of the instrument tip position from the remote center, the term "$\hat{X}'$" is the current direction of the entry guide 200 along the I/O axis (i.e., the longitudinal axis X' of the entry guide 200), "×" is the cross product, and the term "$\hat{X}'_{EG} \dot{q}_{RO,DES} \times \vec{r}_{i,TAN}$" accounts for the additional contribution to velocity due to the fact that the entry guide 200 is rolling about the X' axis.

Figure 13:
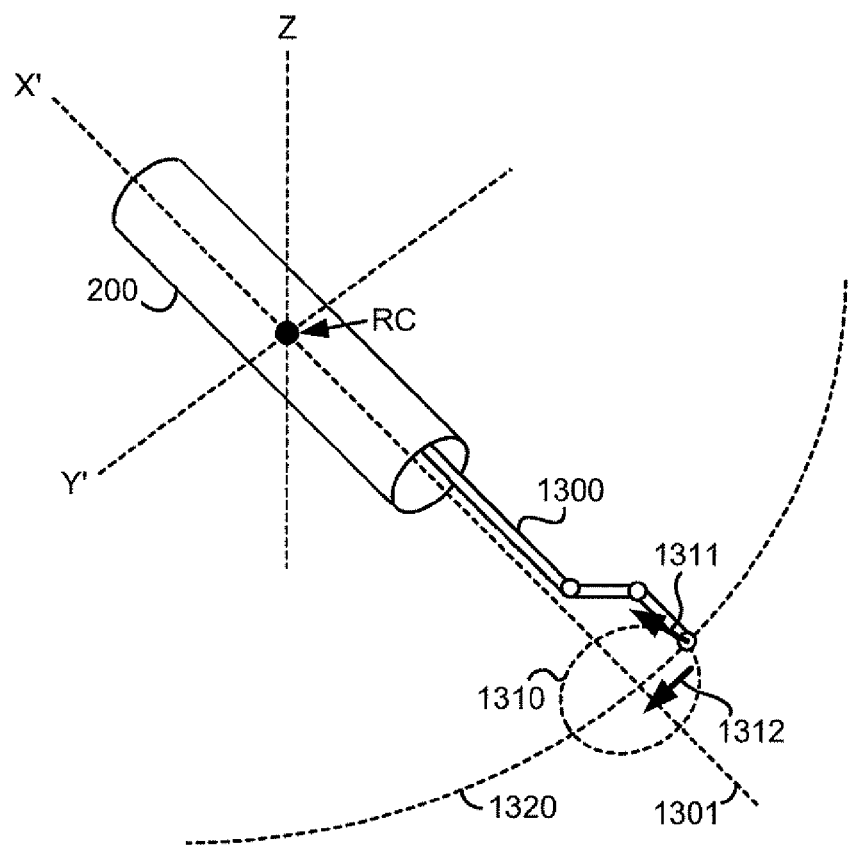
FIG. 13 illustrates a perspective view of an entry guide with angular velocity vectors defined thereon as used in a medical robotic system utilizing aspects of the present invention.

A visual illustration of the resulting vector equation above is shown in FIG. 13 where vector 1311 represents the effect of roll about a circle 1310 having radius equal to the tangential component of the position vector for the instrument 1300, the vector 1312 represents the effect of pitch and yaw about a sphere 1320 having radius equal to the radial component of position vector relative to the remote center for the instrument 1300, and axis 1301 is the EG I/O axis which coincides with the longitudinal axis X' of the entry guide 200.

In 905, the method determines a scale factor to be used for limiting the EGM joint rotary velocities. To do this, it first determines scale factors for each of the instruments 231, 241, 211 using their respective resulting instrument tip velocities according to the following equations:

$$\sigma_1 = \frac{V_{MAX}}{|\vec{V}_{1,DES}|}$$

$$\sigma_2 = \frac{V_{MAX}}{|\vec{V}_{2,DES}|}$$

$$\sigma_{CAM} = \frac{V_{MAX}}{|\vec{V}_{CAM,DES}|}$$

where $V_{MAX}$ is the maximum allowable velocity at the instrument tip.

The scale factor "σ" is then chosen to be the minimum scale factor of all the scale factors calculated for the instruments 231, 241, 211 extending out of the distal end of the entry guide 200.

$$\sigma = \min\{\sigma_1, \sigma_2, \sigma_{CAM}\}$$

In 906, the method applies the scale factor to generate saturated EGM rotary joint velocities. For example, for the EGM yaw joint velocity:

$$\dot{q}_{OY,SAT} = \begin{cases} \dot{q}_{OY,DES} & \text{if } \sigma \geq 1 \\ \sigma \dot{q}_{OY,DES} & \text{if } \sigma < 1 \end{cases}$$

The saturated EGM pitch and roll joint velocities may be similarly determined.

Figure 15:
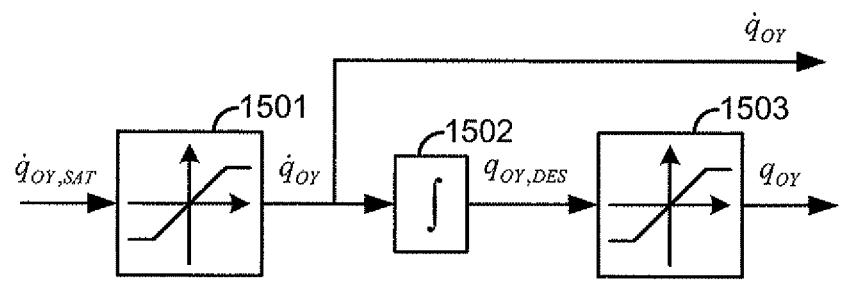
FIG. 15 illustrates a block diagram of an entry guide manipulator yaw joint velocity and position limiting as used in a medical robotic system utilizing aspects of the present invention.

In 907, the saturated EGM rotary joint velocities are then subjected to conventional physical joint position and velocity limits to generate joint commands for actuators which actuate the EGM rotary joints. For example, FIG. 15 illustrates a block diagram for limiting the EGM yaw joint position and velocity in which the saturated EGM yaw joint velocity $\dot{q}_{OY,SAT}$ is limited by a velocity limiter 1501 so that its output $\dot{q}_{OY}$ is less than or equal to the velocity limit for the joint. An integrator 1502 integrates the output $\dot{q}_{OY}$ to generate a desired EGM yaw joint position $q_{OY,DES}$ which is limited by a position limiter 1503 so that its output $q_{OY}$ is less than or equal to a maximum allowable displacement of the EGM yaw joint.

The resulting desired EGM yaw joint velocity $\dot{q}_{OY}$ and position $q_{OY}$ are then provided, for example, as output of the simulated entry guide manipulator block 704 along with a similarly determined EGM pitch velocity and position, similarly determined EGM roll velocity and position, and the previously determined, in 901, EGM I/O velocity and position.

After positioning the entry guide 200, the input devices 108, 109 may be re-associated with their respective surgical tools 231, 241 (as described in reference to FIG. 2). Before such re-association, however, it may be necessary to re-align the orientations of the input devices 108, 109 with their surgical tools 231, 241 to provide a sense of telepresence to the Surgeon. To avoid manual re-alignment by the Surgeon, using a conventional clutch mode for example, the operation of the input devices 108, 109 as a "virtual handlebar" may be taken advantage of to automatically maintain the orientational alignment between the input devices 108, 109 and the surgical tools 231, 241 throughout the entry guide positioning process and therefore, eliminate the need for manual re-alignment prior to such re-association.

One method for automatically maintaining orientational alignment between the input devices 108, 109 and their respective surgical tools 231, 241 is to feedback the surgical tools' sensed orientations to feedback actuators of the input devices 108, 109 to control their orientational degrees-of-freedom (i.e., pitch, roll and yaw rotations about their respective control points 1102, 1112), even while the input devices 108, 109 are associated with the entry guide 200. The remaining translational degrees-of-freedom of the input devices 108, 109 may then be used by the Surgeon to telerobotically position the entry guide 200 in its four degrees-of-freedom through the entry guide manipulator 202.

As an example, input devices 108, 109 may be moved up together in their respective $Z_{LM}$, $Z_{RM}$ axes to pitch the entry guide 200 downward or moved down together to pitch the entry guide 200 upward. Also, the input devices 108, 109 may be moved to the right together in their respective $Y_{LM}$, $Y_{RM}$ axes to yaw the entry guide to the left or moved to the left to yaw the entry guide 200 to the right. The input devices 108, 109 may be moved forward together in their respective $X_{LM}$, $X_{RM}$ axes to move the entry guide 200 forward (in) and moved backward (out) together to move the entry guide 200 backward. Finally, the input devices 108, 109 may be moved in opposite directions in their respective $Z_{LM}$, $Z_{RM}$ axes to roll the entry guide 200 about its longitudinal axis (e.g., moving input device 108 up and input device 109 down to roll the entry guide 200 to the right).

Although the various aspects of the present invention have been described with respect to a preferred embodiment, it will be understood that the invention is entitled to full protection within the full scope of the appended claims.

What is claimed is:

1. A method for positioning and orienting an entry guide that guides a camera and at least one surgical tool through a single entry aperture in a patient to a work site within the patient, the method comprising:

receiving an image referenced command indicative of a desired state of an image relative to eyes of an operator, wherein the image is derived from data provided by the camera and displayed on a display screen so as to be viewable by the operator;

processing the image referenced command to generate a camera command so that a state of a tip of the camera provides the desired state of the image being displayed on the display screen;

processing the camera command to generate an entry guide command so that a state of a distal tip of the entry guide provides the desired state of the image being displayed on the display screen; and processing the entry guide command to generate joint actuator commands so that an entry guide manipulator manipulates the entry guide so that the camera provides data from which the desired state of the image is derived.

2. The method according to claim 1, wherein the processing of the image referenced command to generate the camera command comprises:

adjusting a scale between the image referenced command and the camera command.

3. The method according to claim 2, wherein the image displayed on the display screen is a three-dimensional stereoscopic image, the image referenced command includes left-side and right-side commands received from left and right input devices manipulated by left and right hands of the operator, and the processing of the image referenced command to generate the camera command comprises:

applying offset adjustments to the left-side and right-side commands so as to shift their respective control points so that they respectively correspond to left and right views of the three-dimensional stereoscopic image.

4. The method according to claim 3, wherein the processing of the image referenced command to generate the camera command comprises:

applying offset adjustments to the left-side and right-side commands for aligning the left and right input devices to the eyes of the operator as the operator manipulates the left and right input devices to generate the image referenced control command.

5. The method according to claim 3, wherein the processing of the image referenced command to generate the camera command comprises:

defining a set-point between the control points of the left and right input devices; and generating the camera control using the set-point.

6. The method according to claim 5, wherein the set-point is defined to be a mid-point between the control points of the left and right input devices.

7. A method for positioning and orienting an entry guide that guides a camera to a work site, comprising:

processing and displaying images periodically captured by the camera on a display screen;

disassociating a first input device from a first articulatable tool, and disassociating a second input device from a second articulatable tool;

associating the first and second input devices with the entry guide;

generating an image referenced command from translational movement of the first and second input devices;

positioning and orienting the entry guide in response to the image referenced command;

maintaining orientational alignment between the first input device and the first articulatable tool by feeding back information of an orientation of the first articulatable tool back to the first input device so as to cause orientational movement of the first input device when the first input device and the first articulatable tool are orientationally out of alignment, and maintaining orientational alignment between the second input device and the second articulatable tool by feeding back information of an orientation of the second articulatable tool back to the second input device so as to cause orientational movement of the second input device when the second input device and the second articulatable tool are orientationally out of alignment;

disassociating the first and second input devices from the entry guide; and re-associating the first input device with the first articulatable tool, and re-associating the second input device with the second articulatable tool.

\* \* \* \* \*